United States Patent [19]

Leopold et al.

[11] Patent Number: 4,838,084
[45] Date of Patent: Jun. 13, 1989

[54] DENSITY MEASURING INSTRUMENT

[76] Inventors: Hans Leopold, August-Musgergasse 4, A-8010 Graz; Hans Stabinger, Peterstalstrasse 156, A-8042 Graz, both of Austria

[21] Appl. No.: 238,305

[22] Filed: Aug. 30, 1988

[51] Int. Cl.$^4$ .............................................. G01N 9/00
[52] U.S. Cl. ....................................... 73/32 A; 374/169
[58] Field of Search ...................... 73/32 A, 32 R, 54; 374/142, 169

[56] References Cited

U.S. PATENT DOCUMENTS

| | | | |
|---|---|---|---|
| 3,145,559 | 8/1964 | Banks | 73/32 A |
| 3,177,705 | 4/1965 | Banks | 73/54 |
| 3,218,851 | 11/1965 | Sipin | 73/32 A |
| 3,516,283 | 6/1970 | Abbotts | 73/30 |
| 3,523,446 | 8/1970 | Kratky et al. | |
| 3,775,597 | 11/1973 | November | |
| 3,805,361 | 4/1974 | Miller | |
| 3,842,655 | 11/1974 | Schlatter et al. | |
| 3,910,101 | 10/1975 | Kratky et al. | |
| 4,011,746 | 3/1977 | Weitz, Jr. et al. | |
| 4,132,110 | 1/1979 | Muramoto | |
| 4,215,566 | 8/1980 | Ghahramani | |
| 4,429,564 | 2/1984 | Ikeda et al. | 73/32 A |
| 4,491,009 | 1/1985 | Ruesch | |

Primary Examiner—Daniel M. Yasich
Attorney, Agent, or Firm—Bensutti & Murray

[57] ABSTRACT

A density measurement instrument measures the density of a fluid by determining the frequency of oscillation of a vibrating tube filled with the fluid. An electronic excitation system vibrates the tube and the frequency of oscillation is representative of the density and the temperature. The frequency is accurately measured. A temperature control system controls the temperature of the fluid during oscillation by comparing a single temperature set point with the measured temperature of the sample. Based on this comparison, current in a first direction or in a second direction is applied to a Peltier element for heating or cooling the sample. Substantially continuous temperature readings and adjustments of the current are thus provided. The temperature information may be applied to an external data link or to a display.

9 Claims, 2 Drawing Sheets

DENSITY MEASURING INSTRUMENT

FIELD OF THE INVENTION

This invention relates to the measurement of the density of a fluid in general and in particular to systems for maintaining the fluid at a precise temperature to permit more accurate measurement of the density of the fluid.

BACKGROUND OF THE INVENTION

In density measuring instruments, it is known in the prior art to use a mechanical oscillator, a torsion oscillator or the like which is designed as a vibrator, and which is operatively connected with an apparatus for measuring the frequency and/or the duration of the oscillation by means of electro magnetic, electro dynamic or piezo-electric transducers and the like. The determination of the density is then reduced to a measurement of the resonant frequency of the mechanical oscillator which is filled with the sample. The oscillator, most appropriately, is made of glass and is excited electronically to an undamped oscillation, the frequency of which is dependent upon the mass of the oscillator and therefore upon the density of the sample. In the case of precision measurements, the frequency determination is most favorably achieved by means of a digital counter in connection with a quartz clock.

In order to get a precise measurement in such systems it is known to provide a two-point temperature controller. In this two-point controller type of system two reference points are provided, an upper reference point and a lower reference point. When the temperature of the fluid rises above the upper reference point, the system is cooled to cause the temperature of the fluid to stay within the range between the upper and lower points. When the temperature goes below the lower reference point, heat is put into the system to bring the temperature back up between the upper and lower points. Thus, it may be seen that in such a two-point temperature controller the actual temperature may drift up and down between upper and lower points rather than staying at the desired level for density measurement.

A second problem with such two-point temperature controllers is the lag time between switching the direction of the heat flow and sensing the crossing of the set points. This time lag is due to the thermal time constant of the measuring cell. At high (37° C.) and low (10° C.) measuring temperatures this time lag causes very unsymmetrical excursions of the actual temperature with respect to the set point value.

Thus, it is an object of the present invention to provide a density measuring instrument in which the temperature does not drift up and down between two reference points and is held closely to a predetermined temperature value to permit accurate measurement of density.

It is further object of the present invention to eliminate the lag time between switching and sensing of the crossing of a reference point.

SUMMARY OF THE INVENTION

A density measurement instrument measures the density of a fluid by determining the frequency of oscillation of a vibrating tube filled with the fluid. An electronic excitation system vibrates the tube and the frequency of oscillation is representative of the density and the temperature. This frequency is accurately measured. A temperature control system controls the temperature of the fluid during oscillation by comparing continuously a single temperature set point with the measured temperature of the sample. Based on these comparisons, current in a first direction or in a second direction is applied to a Peltier element for heating or cooling the sample. Substantially continuous temperature readings and adjustments of the current are thus provided. The temperature information may be applied to an external data link or to a display.

DETAILED DESCRIPTION OF THE INVENTION

Figure 1:
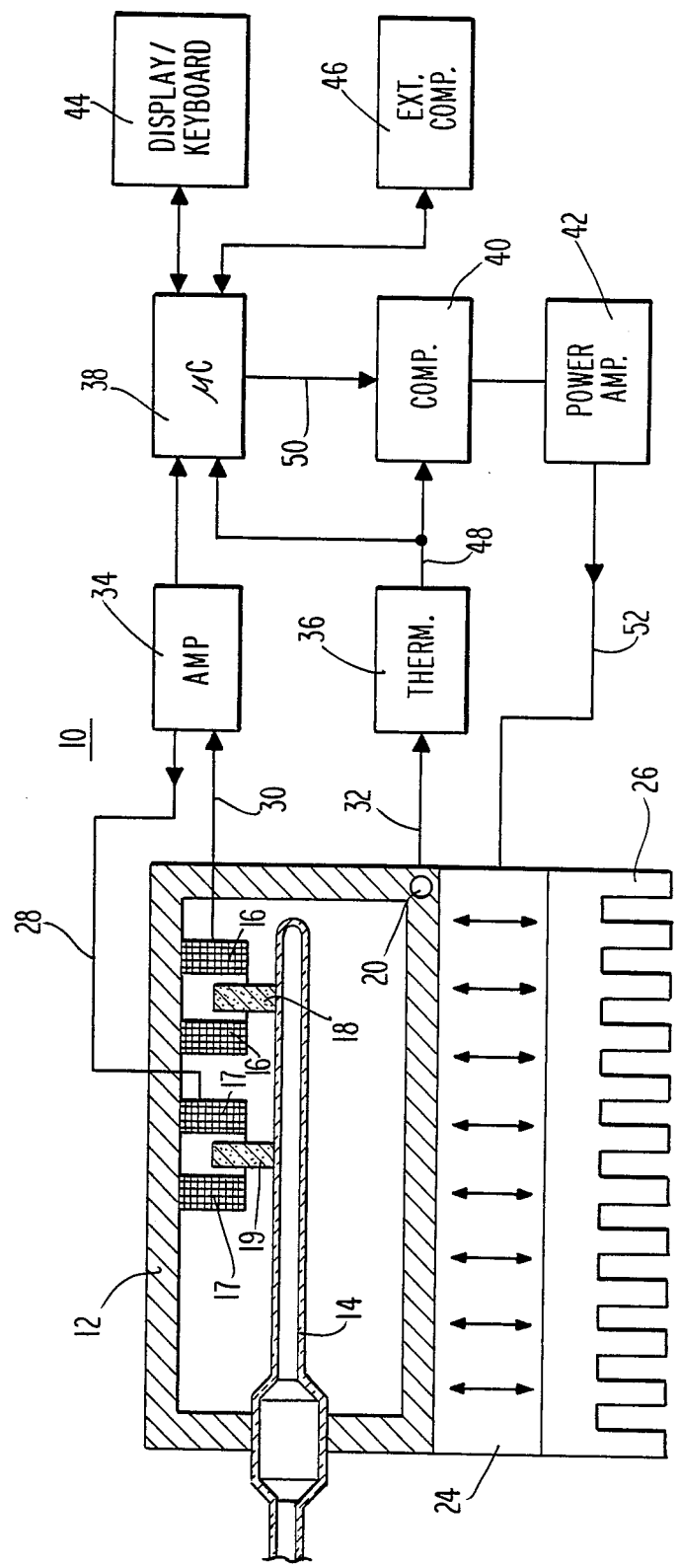
FIG. 1 is a schematic diagram of the density measurement instrument of the present invention.

Referring now to FIG. 1, there is shown density measurement instrument 10 of the present invention. Density measurement instrument 10 includes a U-shaped vibrating glass tube 14 containing a sample for density measurement. Tube 4 is vibrated under the control of excitation amplifier 34. Excitation amplifier 34 senses the motion of tube 14 and measures the frequency of tube 14 by way of line 30 which applies to excitation amplifier 34 signals representative of the relative movement of magnet 18 between coils 16. The signal representative of this motion is amplified by excitation amplifier 34 and excitation amplifier 34 then provides a signal opposite in phase to the phase of the damping force sensed by way of line 30. This opposite phase signal is applied to coils 17 by way of line 28 and acts upon magnet 19 to maintain a precise vibration of tube 14. A system of the type shown is described in U.S. Pat. No. 3,523,446 issued on August 11, 1970 to Kratky at. el., which is incorporated in this detailed description by reference, as if fully set forth herein.

The determination of the density of the sample is reduced to the determination of the resonant or characteristic frequencies of tube 14 which is filled with approximately one cubic centimeter of sample since the frequency of tube 14 is dependent on the overall vibrating mass including the mass of the sample. Thus oscillation measurements within measurement instrument 10 must be very accurate.

Also within excitation amplifier 34 is a period meter (not shown) which precisely measures the period of the oscillations of vibrating glass tube 14 as described. This frequency measurement is performed by counting clock pulses of a crystal oscillator (not shown) during the course of a period of glass tube 14. The period meter includes an Intel 80C31 microcomputer.

Temperature sensor 20 is imbedded within copper block 12 of instrument 10 to determine the temperature of the sample within tube 14. The temperature of copper block 12 is at the measurement temperature of the sample within that vibrating glass tube 14. Thus the electrical signal representative of the temperature sensed by a resistive temperature sensor 20 is also representative of the temperature of the sample within glass tube 14. This electrical signal is applied to electronic thermometer 36 by way of line 32.

Electronic thermometer 36 compares the resistance of resistive temperature sensor 20 to the resistance of a reference resistor (not shown). Temperature sensor 20 is a No. 44031, Yellow Springs Instruments. An integrating analog to digital converter within electronic thermometer 36 digitizes the ratio of the two resistances. The digitized resistance ratio provides information on the temperature of copper block 12 and therefore on the sample within the vibrating tube 14. This temperature information is applied to set point comparator 40 by electronic thermometer 36 by way of line 48. The measuring range of the temperature thus measured is 0°–80° C. with a resolution of 0.01° C.

Microcomputer 38 is an Intel 8052 AH-BASIC system storing information on a single desired reference temperature set point for a sample within vibrating glass tube 14. This single reference temperature set point within microcomputer 38 is applied to set point comparator 40 by way of line 50. The single reference temperature set point within microcomputer 38 may be replaced with a different or further single reference temperature set point so that measurement instrument 10 may be controlled at different temperatures during different measurements. Set point comparator 40 is an adaptive controller consisting of a Siemens SAB 80535 microcontroller which compares the measured temperature received by way of line 48 with the desired temperature set point received by way of line 50 and determines the degree of heating or cooling required to bring the measured temperature to a value equal to the desired temperature. This information on the degree of heating or cooling is applied to power amplifier 42 which applies a positive or negative power signal by way of line 52 to heating and cooling element 24. Heating and cooling element 24 is a bi-directional heat transfer element such as a Peltier effect element 24 made by Marlowe Industries, Inc.

Figure 2:
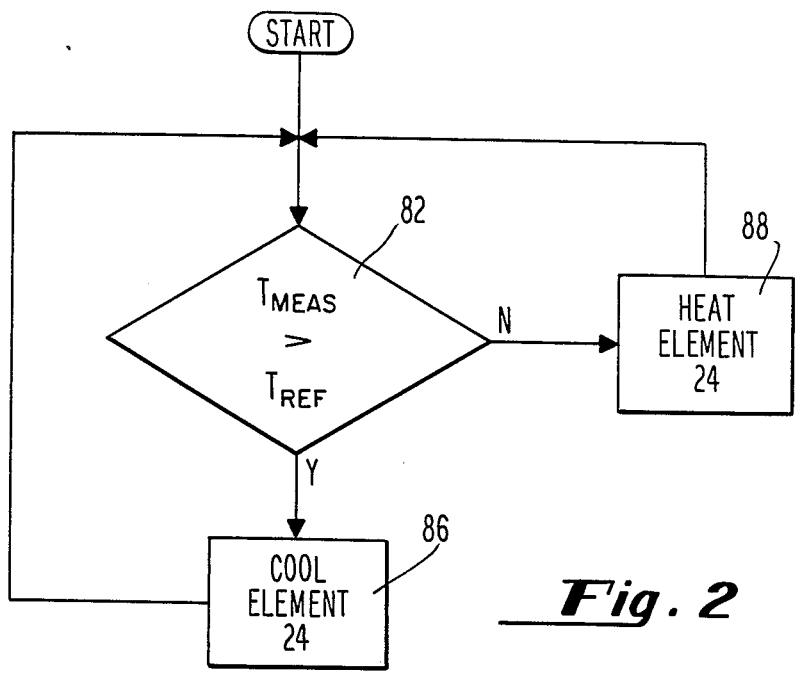
FIG. 2 is a flow chart representation of an algorithm used by the system of FIG. 1 to control the heating of the density measurement instrument of the present invention.

Peltier element 24 is controlled by comparator 40 in a manner described generally by routine 80 shown in FIG. 2. The temperature of tube 14 and copper block 12 as measured by temperature sensor 20 is compared with the reference temperature as shown in decision 82 of routine 80. If the measured temperature is greater than the reference temperature, then element 24 is cooled as shown in block 86. If the measured temperature is less than the reference temperature, element 24 is heated. Thus, a simple too hot/too cold decision is made. Peltier element 24 thus controls the flow of thermal energy into and out of instrument 10 on the basis of the too hot/too cold decision.

In making density measurement instrument 10, element 24 is made into an integral component of density measuring instrument 10. It acts as a heat pump transferring heat in either direction, into or out of instrument 10, depending on the direction of the current flowing through its semiconductor junction. The direction of the current passing through the semiconductor junction of element 24 is controlled in accordance with decision 8 of routine 80. In this way the sample can be heated or cooled with respect to ambient by controlling the direction of the current through element 24. Thus microcomputer 38, thermometer 36, comparator 40, Peltier element 24 and power amplifier 42 act cooperatively to control the temperature of the sample within tube 14.

Figure 3:
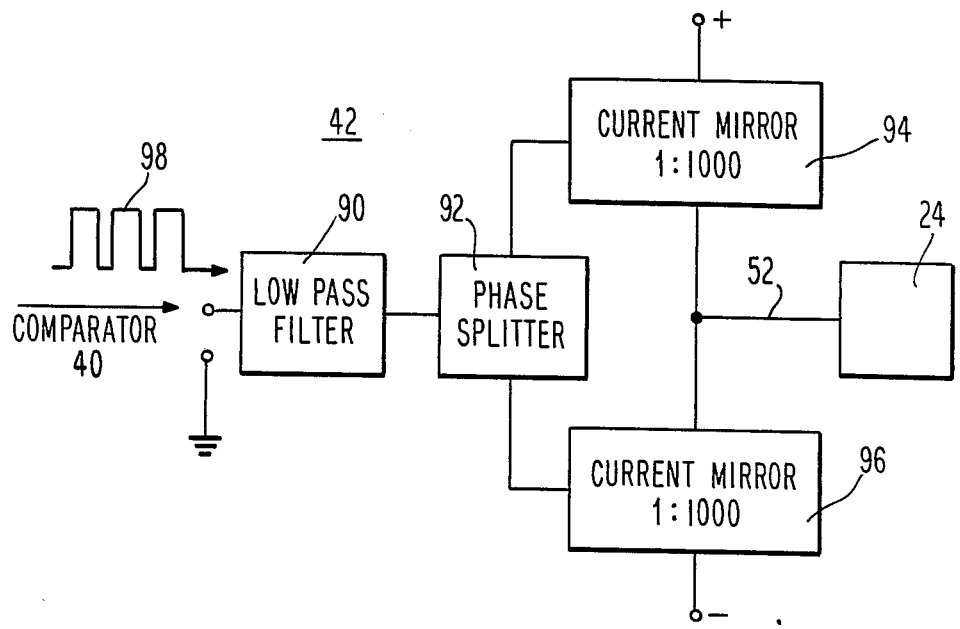
FIG. 3 is a block diagram of a power amplifier of the density measurement instrument of FIG. 1.

Referring now to FIG. 3, power amplifier 42 receives information from temperature comparator 40 by means of a duty cycle modulated signal 98. This signal 98 is low pass filtered by low pass filter 90 of amplifier 42 and split by phase splitter 92 at the fifty percent level of the range into graduated heating or cooling commands. These heating or cooling commands are coded in current. These currents are mirrored and amplified by a factor of 1000 by current mirrors, 94, 96 depending on whether block 86 or block 88 of routine 80 is executed. The amplified signals are then applied to Peltier element 24. Therefore, the amount of heating and cooling is entirely controlled by the commands and not the thermo-electromotive force created by Peltier element 24.

External computer 46 is a commercially available IBM personal computer and includes an external data link which may receive the measured temperature from thermometer 36 and transmit the measured temperature to an external location. Keyboard/display 44 may be used for controlling instrument 10 and the display of keyboard/display 44 may be used to display the temperature determined by electronic thermometer 36.

Digital electronic thermometer 36 along with resistor 2 within block 12 form a very high resolution system (0.01 degrees C). Furthermore the reading of thermometer 36 is updated several times per second within density measurement instrument 10. Thus the current output of power amplifier 42 for controlling power amplifier 42 is able to vary the current to Peltier element 24 very frequently to provide very frequent adjustments of the current applied to element 24. Two hundred fifty six steps are provided between the maximum (full heating) and the minimum (full cooling) within instrument 10 resulting in a substantially continuous and completely smooth relationship of temperature with respect to time. On the other hand the measured actual temperature is processed by the instruments' internal computer in order to select the correct calibration constants, also depending on measuring temperature, and to decide whether the instrument is ready for measurement after warm up. In addition, the continuous controller allows for a much faster transient response shortening the wait after switch-on or after selection of a new measurement temperature.

I claim;

1. An apparatus for measuring the density of a fluid by the determination of the frequency of oscillation of a vibrating tube filled with said fluid, comprising:

mechanical oscillator means wherein the frequency of oscillation is representative of the density and the temperature of the fluid, means for measuring the frequency of oscillation of the oscillator means, temperature control means for controlling the temperature of the fluid during oscillation, the temperature control means including:

single set point means for storing a single reference temperature set point, thermometer means for measuring the temperature of said sample, comparison means for comparing the measured temperature with said single reference temperature set point and determining whether the measured temperature is greater than said single reference temperature set point or less than said single reference set point and providing a comparison signal in response to the comparison, thermal means for both heating and cooling said sample and thermal control means for controlling the thermal means to heat said sample when the measured temperature is below said single reference temperature set point and to cool said sample when said measured temperature is above said single reference temperature set point in response to said comparison signal.

2. The apparatus of claim 1 wherein said thermal means is a Peltier element.

3. The apparatus of claim 1 wherein the thermometer means is a digital thermometer having a substantially high resolution to provide substantially smooth temperature control.

4. The apparatus of claim 2 wherein said thermal control means comprises means for applying current to said thermal means in a first direction when said measured temperature is too high and in a second direction when said measured temperature is too low.

5. The apparatus of claim 4 including means for comparing said temperature frequently for continuously varying the applied current.

6. The apparatus of claim 1 further including an external data link wherein said thermometer means includes means for applying said measured temperature to said external data link.

7. The apparatus of claim 1 further including a display wherein said thermometer means includes means for applying said measured temperature to said display.

8. The apparatus of claim I wherein said comparison means includes means for determining whether said apparatus is ready to perform a measurement.

9. The apparatus of claim 1 including means for replacing said single temperature set point with a further single temperature set point.

* * * * *

UNITED STATES PATENT AND TRADEMARK OFFICE
CERTIFICATE OF CORRECTION

PATENT NO. : 4,838,084

DATED : June 13, 1989

INVENTOR(S) : Hans Leopold, Hans Stabinger

It is certified that error appears in the above-identified patent and that said Letters Patent is hereby corrected as shown below:

Column 3, line 61, reads "8" should read --82--.

Column 4, line 22, the number "2" should read --20--.

Signed and Sealed this

Third Day of April, 1990

Attest:

HARRY F. MANBECK, JR.

*Attesting Officer*  *Commissioner of Patents and Trademarks*